US012208228B2

United States Patent
Ronnander et al.

(10) Patent No.: US 12,208,228 B2
(45) Date of Patent: Jan. 28, 2025

(54) MICRONEEDLE ARRAY COMPRISING A HEAT-PRODUCING ELEMENT

(71) Applicant: LTS LOHMANN THERAPIE-SYSTEME AG, Andernach (DE)

(72) Inventors: James Paul Ronnander, Mount Vernon, NY (US); Andreas Koch, Melsbach (DE)

(73) Assignee: LTS LOHMANN THERAPIE-SYSTEME AG, Andernach (DE)

(*) Notice: Subject to any disclaimer, the term of this patent is extended or adjusted under 35 U.S.C. 154(b) by 690 days.

(21) Appl. No.: 17/436,255

(22) PCT Filed: Mar. 6, 2020

(86) PCT No.: PCT/EP2020/055967
§ 371 (c)(1),
(2) Date: Sep. 3, 2021

(87) PCT Pub. No.: WO2020/178416
PCT Pub. Date: Sep. 10, 2020

(65) Prior Publication Data
US 2022/0143375 A1 May 12, 2022

Related U.S. Application Data

(60) Provisional application No. 62/814,318, filed on Mar. 6, 2019.

(30) Foreign Application Priority Data

Mar. 6, 2019 (DE) .................. 10 2019 105 694.2

(51) Int. Cl.
*A61M 37/00* (2006.01)

(52) U.S. Cl.
CPC . *A61M 37/0015* (2013.01); *A61M 2037/0023* (2013.01); *A61M 2205/0233* (2013.01);
(Continued)

(58) Field of Classification Search
CPC ...... A61M 37/0015; A61M 2037/0023; A61M 2205/0233; A61M 2205/0238;
(Continued)

(56) References Cited

U.S. PATENT DOCUMENTS 5,919,479 A 7/1999 Zhang et al.
2003/0225360 A1 12/2003 Eppstein et al.
(Continued)

FOREIGN PATENT DOCUMENTS

CN 102657914 A 9/2012
CN 108245481 A 7/2018
(Continued)

OTHER PUBLICATIONS

International Preliminary Report on Patentability (Chapter II) received for PCT Patent Application No. PCT/EP2020/055967, mailed on Jun. 21, 2021, 11 pages (6 pages of English Translation and 5 pages of Original Document).
(Continued)

*Primary Examiner* — Amber R Stiles
(74) *Attorney, Agent, or Firm* — Faegre Drinker Biddle & Reath LLP

(57) ABSTRACT

The invention relates to a microneedle array having a heat-generating element and its use for the intradermal application of active ingredients, particularly active pharmaceutical ingredients (API) and drugs, wherein this microneedle array is suitable for skin penetration on humans or animals and the microneedles consist of a water-soluble formulation, which contains at least one active ingredient.

16 Claims, 6 Drawing Sheets

(52) U.S. Cl.
CPC ............... *A61M 2205/0238* (2013.01); *A61M 2205/0294* (2013.01); *A61M 2205/364* (2013.01); *A61M 2205/3653* (2013.01); *A61M 2205/3693* (2013.01)

(58) Field of Classification Search
CPC .... A61M 2205/0294; A61M 2205/364; A61M 2205/3653; A61M 2205/3693; A61M 2037/0046; A61M 2037/0061; A61K 9/0021

See application file for complete search history.

(56) References Cited

U.S. PATENT DOCUMENTS

| | | | | |
|---|---|---|---|---|
| 2005/0153873 | A1* | 7/2005 | Chan | A61K 31/4172 |
| | | | | 514/9.9 |
| 2008/0009800 | A1* | 1/2008 | Nickel | A61M 37/0015 |
| | | | | 604/20 |
| 2008/0208162 | A1* | 8/2008 | Joshi | A61M 37/0015 |
| | | | | 604/291 |
| 2009/0035446 | A1 | 2/2009 | Kwon | |
| 2010/0305473 | A1* | 12/2010 | Yuzhakov | A61M 37/0015 |
| | | | | 604/173 |
| 2014/0066842 | A1* | 3/2014 | Zhang | A61P 43/00 |
| | | | | 604/512 |
| 2018/0236215 | A1 | 8/2018 | Liu et al. | |

FOREIGN PATENT DOCUMENTS

| | | |
|---|---|---|
| CN | 108744261 A | 11/2018 |
| CN | 108853709 A | 11/2018 |
| DE | 10353629 A1 | 6/2005 |
| JP | 2013-215592 A | 10/2013 |
| JP | 2018-135286 A | 8/2018 |
| KR | 10-2010-0034836 A | 4/2010 |
| KR | 10-2018-0002233 A | 1/2018 |
| KR | 2018-0003286 A | 1/2018 |
| KR | 10-2018-0011653 A | 2/2018 |
| KR | 10-1847984 B1 | 4/2018 |
| KR | 10-2018-0079728 A | 7/2018 |
| WO | 2016/162449 A1 | 10/2016 |

OTHER PUBLICATIONS

International Search Report and Written Opinion received for PCT Patent Application No. PCT/EP2020/055967, mailed on Jul. 9, 2020, 10 pages (2 pages of English Translation and 8 pages of Original Document).

* cited by examiner

Figure 2:
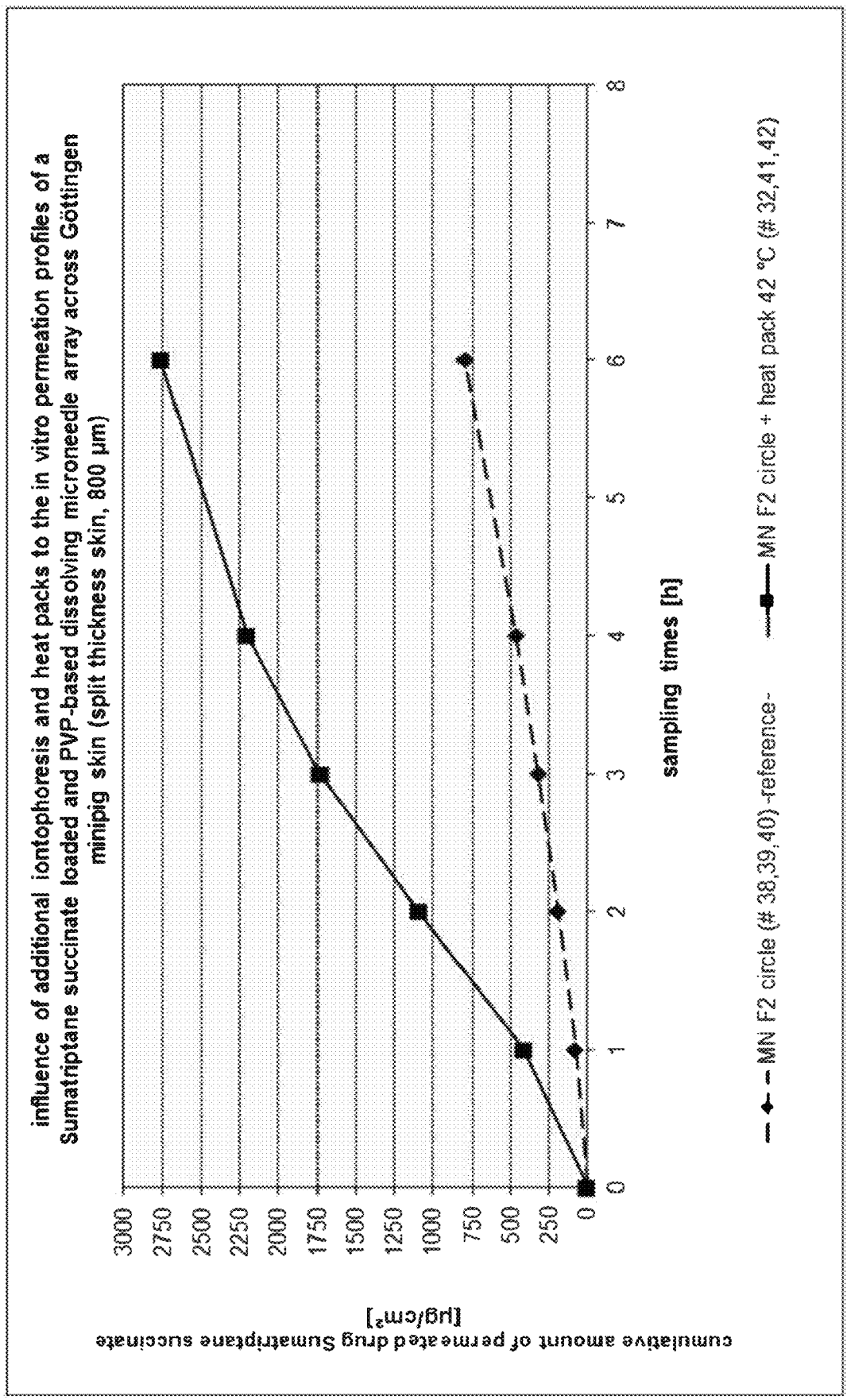

Figure 2: influence of additional iontophoresis and heat packs to the in vitro permeation profiles of a Sumatriptane succinate loaded and PVP-based dissolving microneedle array across Göttingen minipig skin (split thickness skin, 800 μm)

Figure 3:
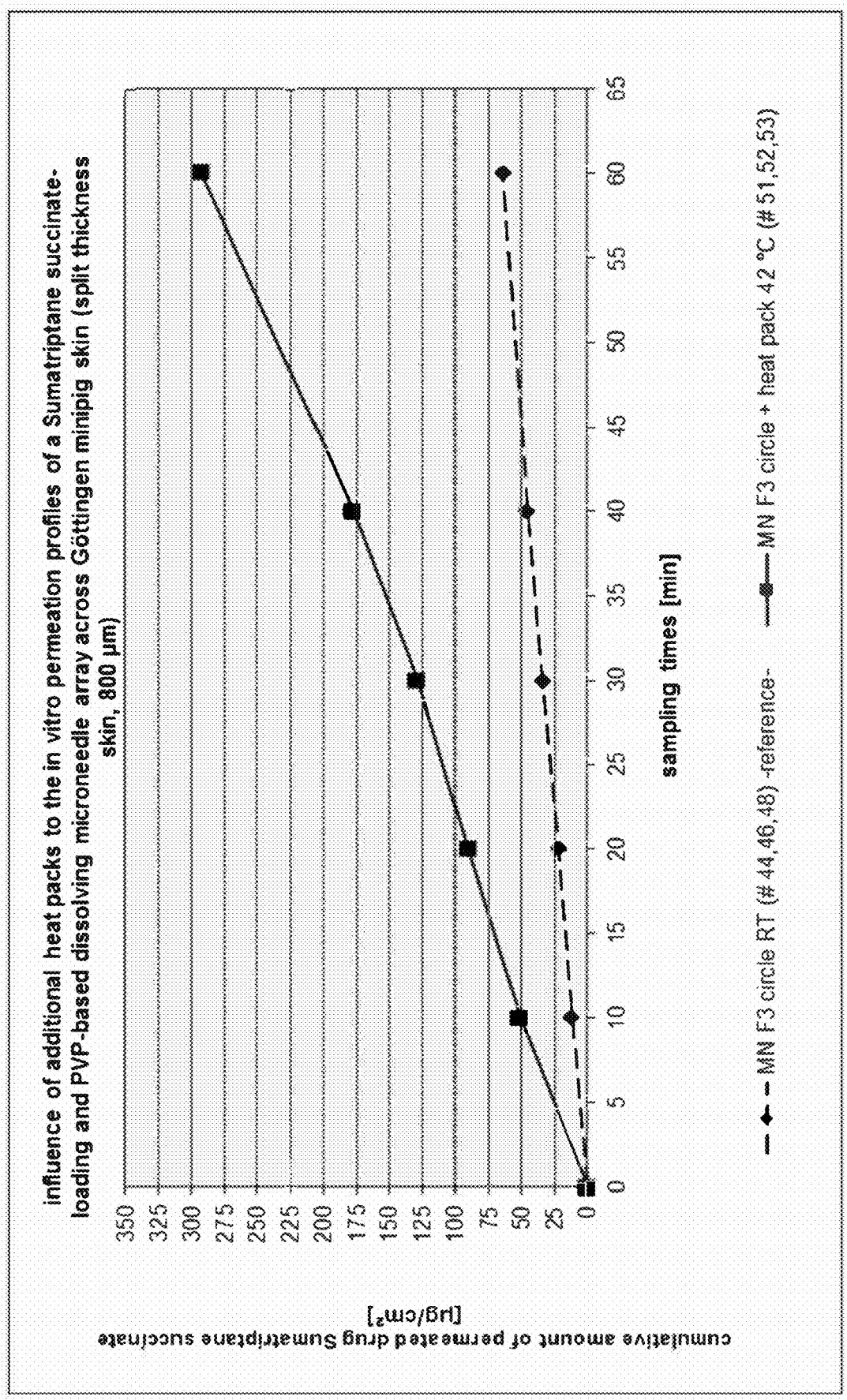

Figure 3: influence of additional heat packs to the in vitro permeation profiles of a Sumatriptane succinate-loading and PVP-based dissolving microneedle array across Göttingen minipig skin (split thickness skin, 800 μm)

MICRONEEDLE ARRAY COMPRISING A HEAT-PRODUCING ELEMENT

CROSS-REFERENCE TO RELATED APPLICATIONS

This application is a national stage application (under 35 U.S.C. § 371) of PCT/EP2020/055967, filed Mar. 6, 2020, which claims benefit of German Application No. 10 2019 105 694.2, and U.S. Application No. 62/814,318, both filed Mar. 6, 2019, and all of which are incorporated herein by reference in their entirety.

The invention relates to a microneedle array having a heat-generating element and its use for the intradermal application of active ingredients, particularly active pharmaceutical ingredients (API) and drugs, wherein this microneedle array is suitable for skin penetration on humans or animals and the microneedles consist of a water-soluble formulation, which contain at least one active ingredient.

The skin consists of several layers. The outermost layer of skin, the stratum corneum, has known barrier properties to prevent foreign substances from entering the body and intrinsic substances from escaping from the body. The stratum corneum, which is a complex structure of compacted keratotic cell residues having a thickness of approximately 10-30 micrometers, forms a waterproof membrane to protect the body. This natural impermeability of the stratum corneum prevents the administration of most pharmaceutical agents and other substances through the skin as part of an intradermal application.

Various substances are therefore administered, for example, by creating micropores or incisions in the stratum corneum and supplying or applying a drug in or under the stratum corneum. For example, numerous drugs can also be administered subcutaneously or intradermally or intracutaneously in this way.

Microneedle systems (short: MNS) and devices in which microneedle arrays (short: MNA) are used for the painless intradermal (or transdermal) administration of active ingredients, particularly drugs, are known in the prior art, as described, for example, in WO2016/162449A1 by the applicant. The disadvantage, however, is that the dwell time after application is too short after the application of external force in the skin. The frictional connection is too short in time, the MNS detach themselves too quickly from the skin and consequently the further release of the active ingredient can be interrupted. So-called self-dissolving and API-loaded MNS (so-called "drug loaded and self-dissolving microneedle arrays") were developed in order to compensate for this disadvantage. This type of MNS does not require an extra API storage container (depot) or a retaining device for the MNS, as described, for example, in WO2016/162449A1.

The only requirement is that the microneedles are able to completely penetrate the stratum corneum as the outermost skin layer and main permeation barrier and, due to their composition, to dissolve completely. The necessary dissolution speed—especially for a quick onset of action—should be as high as possible. This mainly depends on the skin type of the patient; the water content in the upper skin layer (epidermis) is particularly decisive and varies greatly depending on the skin type. Dry skin has a lower water content than oily skin, and consequently the dissolution speed and the so-called lag time, that is, the time from which a uniform diffusion flow and thus the beginning of the therapeutic effect occurs, can be different. Since the carrier matrix of the microneedle array usually consists of polymers that are not very stable mechanically, such as polyvinylpyrrolidone (PVP) or poly (lactide-co-glycolide) (PLGA), the effective delivery area is limited. This is particularly a problem if the required therapeutic release rate of the API cannot be achieved due to the MNS, which is limited in area, since it is too low for the intended indication.

There is therefore a need from the prior art to be able to apply active ingredients intradermally effectively and largely independently of the skin type.

The objective task of the invention is therefore to provide a suitable microneedle array for the intradermal application of active ingredients, wherein the lag time (supra) is shortened.

The objective task can also be formulated in such a way as to accelerate the dissolution process of the microneedle array and consequently to advantageously increase the amount released and the rate of release of the active ingredient which has permeated or is released from the MNS.

The problem is solved by the conveyed technical teaching of the patent claims.

The invention therefore relates to one having the features of claim 1, namely a microneedle array for use in intradermal application, wherein the microneedles contain a substantially water-soluble formulation containing at least one active ingredient and the microneedle array has at least one heat-generating element.

It is particularly advantageous that the penetrated microneedles are at least partially dissolved in situ under the influence of heat and can be resorbed immediately.

Any active ingredients which are suitable for intradermal administration are included according to the invention. Suitable active ingredients or active ingredient groups/classes cannot be conclusively those such as hypnotics, sedatives, antiepileptics, wake amines, psychoneurotropics, neuro-muscle blockers, antispasmodics, antihistamines, antiallergics, cardiotonics, antiarrhythmics, diuretics, hypotensives, vasopressants, antitussives, expectorants, analgesics, thyroid hormones, sex hormones, glucocorticoid hormones, antidiabetic agents, antitumor agents, antibiotics, chemotherapeutic agents, narcotics, anti-Parkinson agents, anti-Alzheimer's agents, triptans or vaccine serums.

In a water-soluble formulation, the active ingredient can, for example, preferably be positioned at the tip of the needles, or the active ingredient can be the subject of a coating made from a water-soluble formulation. Coating means that the microneedles have an outer layer, such as a jacket, which can be applied.

In a preferred embodiment, the invention therefore relates to a microneedle array for use in intradermal application, wherein the water-soluble formulation containing at least one active ingredient is present in the tip of the microneedles and/or is part of a coating.

Therefore, the need for the microneedles to be hollow on the inside or to have a channel is also advantageously dispensed with, because the active ingredient, embedded in a formulation is introduced into the skin and released.

A microneedle array according to the invention having a heat-generating element can be implemented in several preferred embodiments, as a result of which the release amount and the release rate of permeated or released active ingredient are advantageously increased from the water-soluble formulation.

A preferred embodiment therefore relates to a microneedle array having a heat-generating element, wherein the microneedle array contains a heat store, particularly a latent heat store. Such an embodiment is shown as an example in FIG. 1.

In a preferred embodiment, the heat can be generated in a heat store by chemical oxidation reaction, such as atmospheric oxygen with pyrophoric iron on activated carbon in the presence of water or by physicochemical processes, such as the release of crystallization heat after recrystallization from a supersaturated solution. Such a device is generally referred to as a heating pad or heat pack (see, for example, U.S. Pat. No. 5,919,479).

The invention therefore also relates to a microneedle array having a heat-generating element which contains an electrically conductive, textile fabric in which electrically conductive fibers are in contact with one another and heat can be generated by supplying an external or internal power source.

However, the prior art does not describe the use of such heat packs for accelerated dissolution of a carrier matrix, particularly a water-soluble formulation containing an active ingredient. Other latent heat stores or external heat-generating sources can be electrically heatable textile fabrics, sheet-like piezoelectric foils that generate ultrasound and are based on the inverse piezo effect, for example, foils made of polyvinylidene fluoride.

Therefore, a preferred embodiment relates to a microneedle array having a heat-generating element, wherein a piezoelectric film, preferably made of polyvinylidene fluoride (for example, Kynar™ Piezo Film from Pennwalt Corp., Valley Forge, USA), is placed on the skin to be treated phonophoretically using an ultrasound generator preferably covering 70% of the area. The ultrasonic generator to be used can be provided, for example, from a kit for tone generators (for example, Kit No. 0-182 from Kemo Electronic GmbH, Geestland, Germany). The tone generator converts an applied direct current into a pulsating direct current, which can be viewed as "pseudo-alternating current". This, in turn, is the necessary prerequisite for generating ultrasonic waves from a piezoelectric film by means of the inverse piezoelectric effect, which at the same time generate heat, depending on the intensity or power of the system used. In an arrangement according to the invention, the temperature generated is 37° C., which is already sufficient for a detectable effect of the acceleration of the amount of active ingredient which has permeated or is released from a pharmaceutical dosage form.

The invention therefore also relates to a microneedle array having a heat-generating element which contains an ultrasound transmitter together with an electrically conductive piezo film and heat can be generated by supplying an external or internal power source.

It is preferred that the heat of a heat-generating element is higher than the body temperature, particularly 42-50 degrees Celsius.

In a further embodiment of the invention, the heat generated can be held for 2, 4 or 6 hours.

In a preferred embodiment, the heat-generating element, particularly a heat store, can be designed as the top cover ("backing layer") of a microneedle array.

The microneedle array can have a plurality of microneedles in order to be able to deliver an active ingredient via the skin or into the skin of a patient, wherein the microneedle array is applied to the skin of the patient. Each of the microneedles of the microneedle array preferably has an elongated shaft with two ends, the one end of the shaft is the base of the microneedle with which the microneedle is fastened to the flat carrier or with which the microneedle is integrated into the flat carrier. The end of the shaft opposite the base is preferably designed to taper to a point in order to enable the microneedle to penetrate the skin as easily as possible.

The microneedle array according to the invention is suitable for use in intradermal application of an active ingredient and comprises a plurality of microneedles on a carrier, wherein the microneedles contain a substantially water-soluble formulation which can have at least one active ingredient.

The substantially water-soluble formulation can particularly preferably be those formulations which have at least one water-soluble polymer, preferably those polymers selected from the group consisting of polyvinylpyrrolidone, polyvinyl alcohols, cellulose, dextrans, alpha-hydroxy acids, such as lactic acid and/or glycolic acid, polylactides, polyglycolides, polylactide-co-glycolides, and copolymers thereof with polyethylene glycol, polyanhydrides, poly(ortho)esters, polyurethanes, polybutyric acids, polyvaleric acids, and polylactide-co-caprolactones.

For the purposes of this invention, those polymers are also water-soluble which dissolve up to 50% in water or ethanol or alcohol-water mixtures at room temperature or up to 80% at the boiling point, that is, at approx. 78° C.

The microneedles can have a shaft having a round cross-section or a non-round cross-section, for example, having a triangular, square or polygonal cross-section. The shaft can have one or more passages that run/s from the needle base to the needle tip or approximately to the needle tip. The microneedles can be designed as (barbed) hooks, wherein one or more of these microneedles has one or more such hooks. Furthermore, the microneedles can be designed in a helical manner and rotatably arranged, thereby facilitating penetration into the skin and anchoring it in the skin when a rotating movement is used (DE 103 53 629 A1), particularly at the desired depth of penetration in the epidermis.

The diameter of a microneedle is usually between 1 µm and 1000 µm, preferably between 10 µm and 100 µm. The diameter of a passage is usually between 3 µm and 80 µm and is suitable for the passage of preferably liquid substances, solutions and substance preparations. The length of a microneedle is usually between 5 µm and 6,000 µm, particularly between 100 µm and 700 µm.

The base of the microneedles is fastened to a flat carrier or integrated into a flat carrier. The microneedles are preferably arranged so as to be substantially perpendicular to the surface of the carrier. The microneedles can be arranged regularly or irregularly. An arrangement of a plurality of microneedles can have microneedles having different cross-sectional shapes, differently dimensioned diameters and/or different lengths. The arrangement can also comprise solid microneedles, and partially solid composites.

The density of the microneedles on a carrier can be 5-5,000 pieces/cm$^2$, particularly 5-1,000 pieces/cm$^2$.

The microneedle array can have a flat carrier, wherein the carrier substantially has a disk-shaped, plate-shaped or film-shaped basic shape. The carrier can have a round, oval, triangular, square or polygonal base. The carrier can be made from different materials, for example, from a metal, a ceramic material, a semiconductor, an organic material, a polymer or a composite. Preferably foils or web-like materials can be mentioned as materials that are suitable for the production of the carrier, for example, microporous membranes, preferably made of polyethylene (PE) or polypropylene (PP), or diffusion membranes, preferably made of ethylene-vinyl acetate copolymer (EVA) or polyurethane (PUR). Suitable materials for producing the carrier can be selected from the group comprising polyesters such as polyethylene terephthalates (PET), polycarbonates (PC), polyether ketones (PAEK), polyethylene naphthalate (PEN), polybutylene terephthalate (PBT), polyurethanes (PU), polystyrenes (PS), polyamides (PA), polyoxymethylene (POM), polyolefins such as polyethylene (PE) and polypropylene (PP), polytetrafluoroethylene (PTFE), polyvinyl chloride (PVC), polyvinylidene chloride (PVDC), polylactate (PLA), polymethyl methacrylate (PMMA) and cellulose-based plastics such as cellulose hydrate or cellulose acetate. Suitable materials for producing the carrier can also be selected from the group of metals which comprise aluminum, iron, copper, gold, silver, platinum, alloys of the aforementioned metals and other pharmaceutically acceptable metal foils or foils coated with metal.

The carrier is preferably made of a flexible material, for example, a plastic. A carrier made of a flexible material can adapt better to the skin surface and its curvature than a carrier made of a non-flexible material. As a result, better contact of the microneedle array with the skin is achieved, resulting in the reliability of the microneedle array being improved.

In a preferred embodiment, the microneedle array is a flat or planar microneedle array.

In a further embodiment, the microneedle array according to the invention can be configured with a heat-generating element with customary functional objects that allow fixing on the skin, and easy handling for exerting pressure on the skin and particularly can contain at least one fixing means. According to a further embodiment, the microneedle array can contain fixing means, which are preferably fastened to the skin of a patient or test person with the aid of a pressure-sensitive adhesive strip or plaster, also called needle plasters. Highly viscous substances that stick to the skin after a short, gentle pressure, so-called pressure-sensitive adhesives (PSA), are suitable as pressure-sensitive adhesives. They have high cohesive and adhesive forces. For example, pressure-sensitive adhesives based on poly(meth)acrylates, based on polyisobutylenes or based on silicones can be used. In a further embodiment, the fixing means can consist of a tape, elastic band, rubber or belt. A secure fastening to the body can take place with the aid of such fixing means. If necessary, the microneedle array having a heat-generating element can be connected to an external or internal power source.

The term "intradermal application" (synonym: "intracutaneous application") according to the invention describes the administration of any active ingredients into the skin via the microneedle array and requires the microneedles to prick or penetrate into the skin.

The invention further relates to the use of a microneedle array having a plurality of microneedles on a carrier, wherein the microneedles contain a substantially water-soluble formulation containing at least one active ingredient and the microneedle array has a heat-generating element for purposes of intradermal application.

The following examples and figures serve to explain the invention further, but without restricting the invention to these examples.

EXAMPLE 1

1. Production of Microneedle Systems

Sumatriptan succinate, polyvinylpyrrolidone (PVP), polysorbate 80 and glycerin were dissolved in water according to Table 1 in different proportions.

The various solutions were poured into needle-negative matrices made of silicone, the surface of which was vapor-coated with a thin layer of platinum. The negative matrices were dried with the various solutions overnight at room temperature. The dried microneedle systems were then carefully pressed out of the matrices and stored in special PE containers that were moisture-proof until further use.

Prior to use in the in vitro permeation studies, random samples of the samples produced were examined analytically for their target active ingredient content, optically for their completeness and uniformity with regard to the microneedles and mechanically for their sufficient strength. In addition, an efficiency test was carried out with regard to sufficient perforation by measuring the transepidermal water loss (TEWL) before and after treatment. For sufficient perforation, the microneedle systems used should show at least one difference (before and after perforation) in the TEWL value of 40 $g/m^2 \times h$.

TABLE 1

Composition of the various microneedle systems (in weight %)

| Formulation | Water | Sumatriptan succinate | PVP | Polysorbate 80 | Glycerin |
|---|---|---|---|---|---|
| F1 | 58 | 10 | 30 | 1 | 1 |
| F2 | 63 | 5 | 30 | 1 | 1 |
| F3 | 73 | 5 | 20 | 1 | 1 |

2. Preparation of the Skin for the In Vitro Permeation Studies

The back part of Gottinger Minipighaut (Ellegaard Göttingen Minipigs Agricultural Service, Dalmose, Denmark) was used as the skin. The skin, which is delivered as a so-called full skin without subcutaneous fatty tissue in a frozen state, must first be thawed at room temperature and carefully shaved with plenty of water without using any shaving foam to remove the bristles. The skin is then dermatomized or cut to a layer thickness of 800 µm with the aid of an Acculan 3TI battery-powered electric dermatome (Aesculap AG, Tuttlingen, Germany). Circular punched pieces having a diameter of 25 mm are then knocked out of the pieces of skin treated in this way with the help of a corresponding punching tool, for example, a handle punch and are stored shrink-wrapped in PE bags until further use at −20 degrees Celsius (maximum storage period under these conditions up to 12 months).

3. Performing the In Vitro Permeation Studies

The permeation studies were performed in static and vertical Franz cells (Glastechnik Gräfenroda, Germany) with a diffusion area of 1.595 $cm^2$ and an acceptor volume of 10 ml. The acceptor medium used was phosphate buffer having a pH value of 7.4 according to DAB 10, tempered to 32° C. during the entire permeation time and constantly stirred for uniform mixing of the permeated active ingredient. The acceptor medium was completely replaced by fresh one at the scheduled sampling times. Before the pre-prepared skin punches are clamped in the Franz cells and filled with acceptor, the microneedle systems must first be pressed into the top layer of skin using a manufactured pressure adapter, in the sense of a nail gun with an impulse strength of 150 $N/cm^2$.

Before filling with the acceptor and inserting the Franz cells into the water bath controlled to a temperature of 32° C., the temperature-controlled cell heads are put on or they are prepared with an active heat pack mixture, see also the figures including explanations.

4. Analytical Determination of Sumatriptan Succinate in the Acceptor Samples

The analytical determination was carried out by means of HPLC on a C18-Inertsil separation column (250×4.6 mm, 5 µm particle size; VDS Optilab, Berlin) by means of UV detection at 282 nm and at 30 degrees Celsius. A mixture consisting of acetonitrile, methanol and 0.02167 m sodium dihydrogen phosphate solution 10:20:85 (v %/v %/v %) and a pH of 3.2 was used as the eluent. The flow rate was 1.0 ml/min and 20 µl were injected.

The present examples can be performed analogously for other active ingredients.

Figure 5:
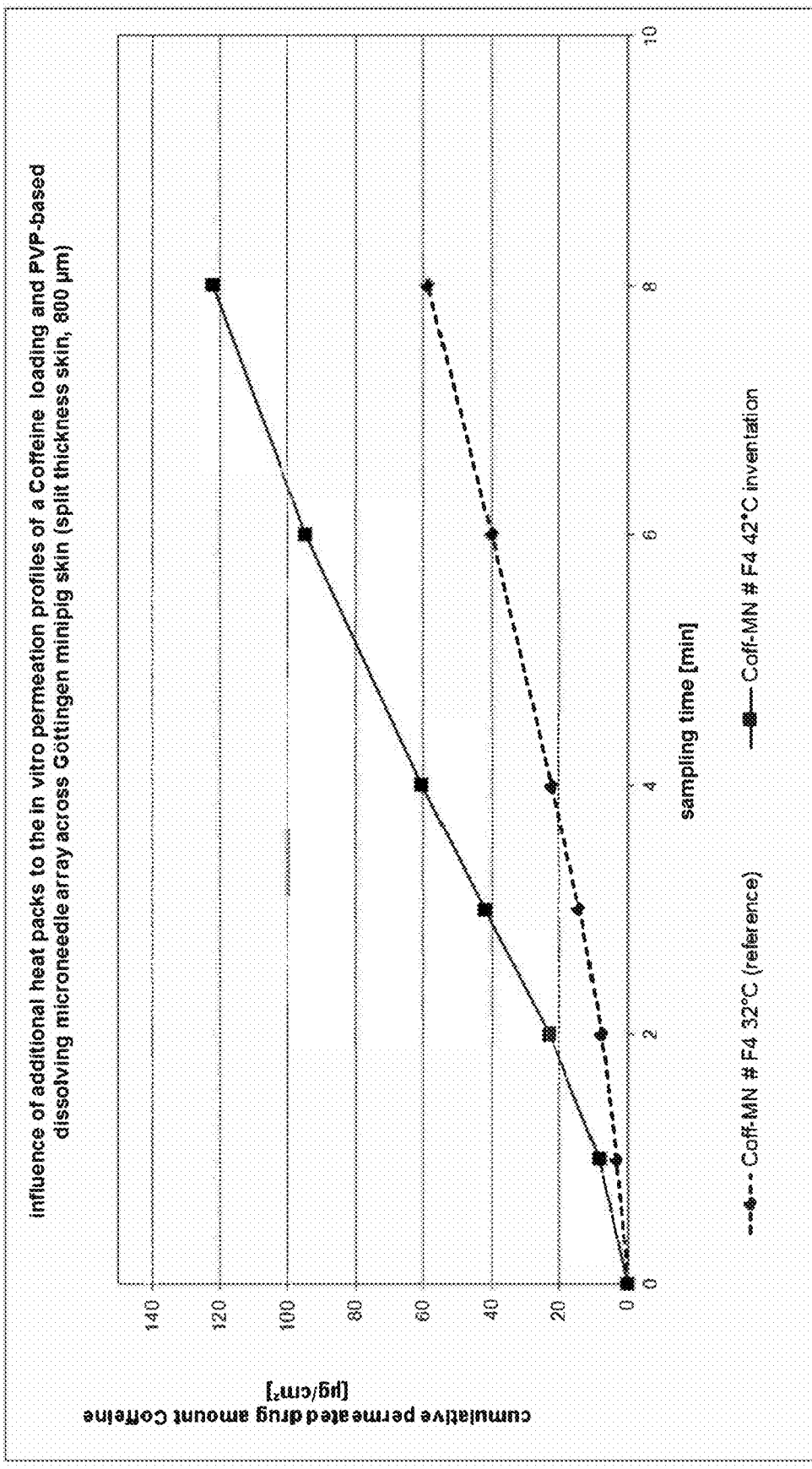

FIG. 5 shows, for example, the analogous performance with the active ingredient caffeine. The composition of the microneedle system is given in Table 2.

TABLE 2

Composition of the microneedle system (in weight %) with the active ingredient caffeine

| Formulation | Water | Caffeine | PVP | Na alginate | Glycerin |
|---|---|---|---|---|---|
| F4 | 77 | 1 | 20 | 1 | 1 |

5. Analytical Determination of Caffeine in the Acceptor Samples

The analytical determination was carried out by means of HPLC on a C12-Synergi-Max-RP separation column (150× 4.6 mm, 4 µm particle size; Phenomenex, Aschaffenburg) by means of UV detection at 273 nm and at 25 degrees Celsius. A mixture consisting of methanol and HPLC water 40:60 (v %/v %) was used as an eluent. The flow rate was 1.0 ml/min and 20 µl were injected.

FIGURES

Figure 1:
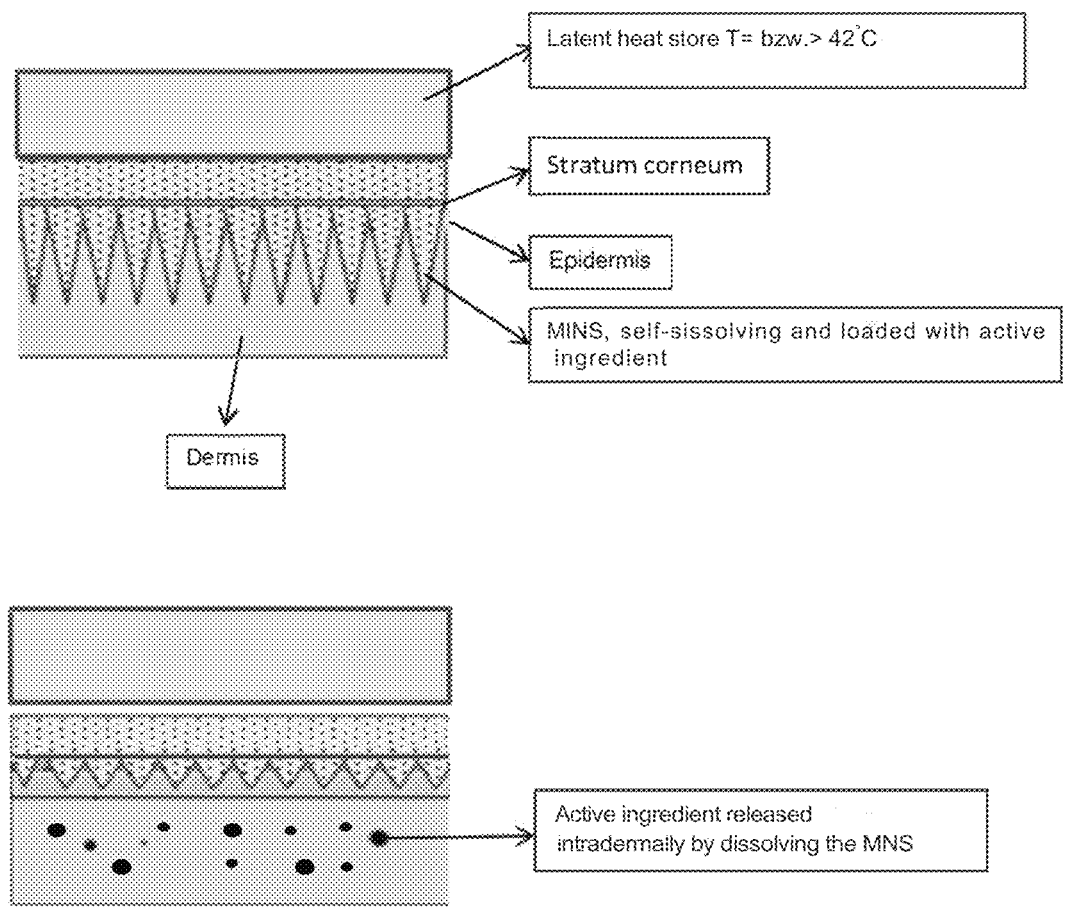

FIG. 1: FIG. 1 shows the use of a heat store.

FIG. 2: Comparison of example 1 according to the invention with external heat generation in comparison to the reference system without additional heat generation in a period up to 6 hours. Both experiments were performed in a FRANZ cell. The heat was generated by means of a heatable (thermostated water) cell head specially designed for the FRANZ cell used (=heat store, so-called heat pack). The lag time of the inventive example is 20 minutes, while that of the reference is 40 minutes, that is, is larger by a factor of 2, which is then also associated with a later onset of action. The amount or rate of release of API, here sumatriptan succinate, of the inventive example is here approximately a factor of 5 greater than that of the reference.

FIG. 3: Comparison of a further example according to the invention with external heat generation in comparison to the corresponding reference system without additional heat generation within a period of 60 minutes. Both experiments were carried out in a FRANZ cell. The heat was generated by means of a heatable (thermostated water) cell head specially designed for the FRANZ cell used (=heat store, so-called heat pack). The lag time of the inventive example is 0.5 minutes, while that of the reference is 1.0 minutes, that is, is larger by a factor of 2, which is then also associated with a later onset of action. The amount or rate of release of API, here sumatriptan succinate, of the inventive example is here approximately a factor of 4 greater than that of the reference.

Figure 4:
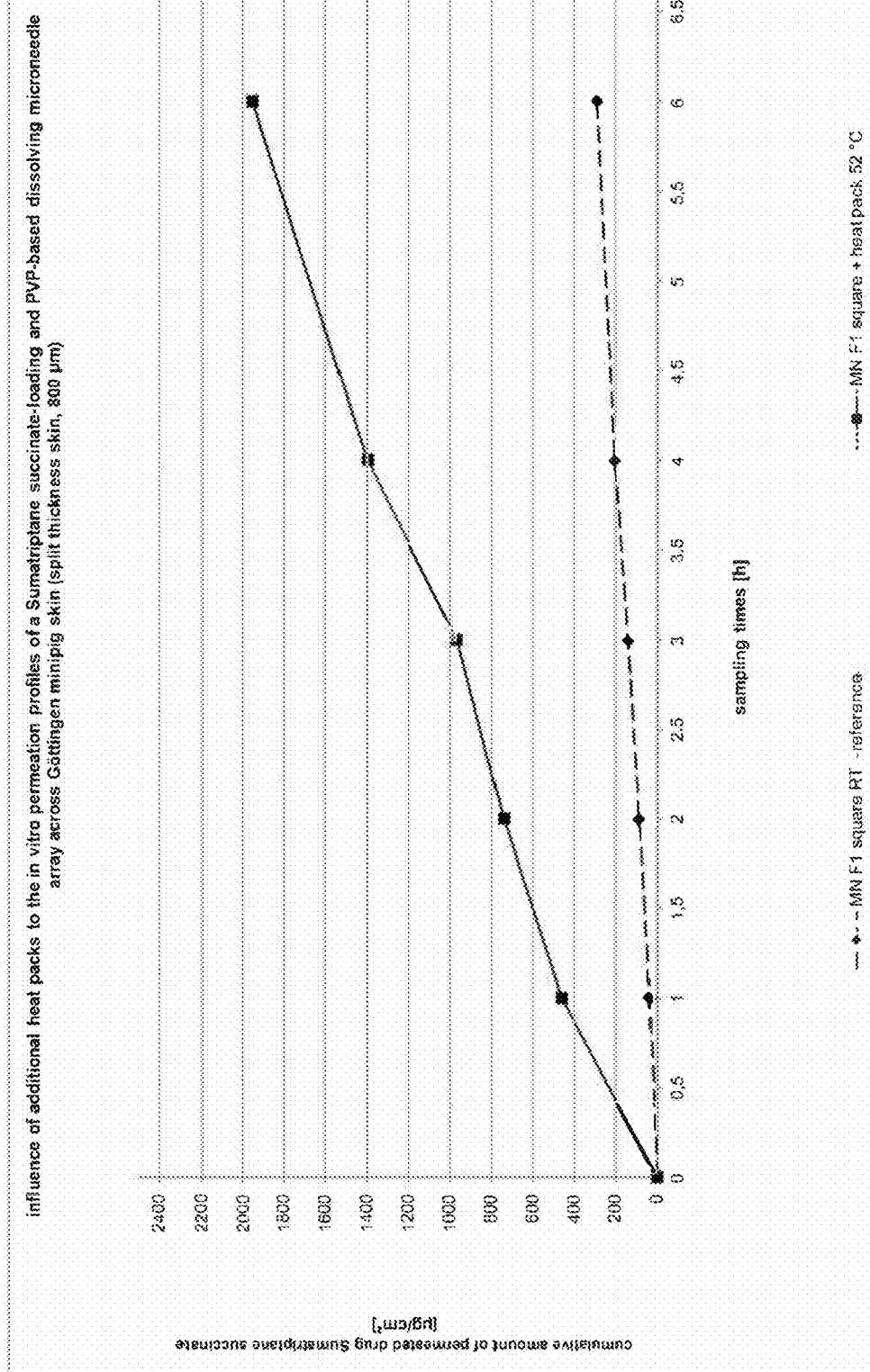

FIG. 4: Comparison of a further example according to the invention with external heat generation in comparison to the corresponding reference system without additional heat generation within a period up to 6 hours. Both experiments were carried out in a FRANZ cell. The heat was generated by means of a commercial heat pack (Thermopad from Thermopad GmbH from Freudenstadt, Germany). The heat pack used had a heat-generating mixture of pyrophoric iron, activated carbon and sodium chloride in a ratio of 16:3:3 percent by weight each and was started catalytically by small amounts of water, in the present case 50 µl (part of the content, 1700 mg, of the commercial heat pack was transferred to the head of the Franz cell used, wherein this head, in a special embodiment made of polypropylene, was provided with lateral opening holes for sufficient oxygen access). The lag time of the inventive example is 0.1 minutes, while that of the reference is 0.4 minutes, that is, is larger by a factor of 4, which is then also associated with a later onset of action. The amount or rate of release of API, here sumatriptan succinate, of the inventive example is approximately a factor of 8 greater than that of the reference.

FIG. 5: Comparison of a further example according to the invention with external heat generation in comparison to the corresponding reference system without additional heat generation within a period of 8 hours. Both experiments were carried out in a FRANZ cell. The heat was generated by means of a heatable (thermostated water) cell head specially designed for the FRANZ cell used (=heat store, so-called heat pack). The lag time of the inventive example is 40 minutes, while that of the reference is 100 minutes, that is, is larger by a factor of 2.5, which is then also associated with a later onset of action. The amount or rate of release of API, here caffeine, of the inventive example is here approximately a factor of 2 greater than that of the reference.

Figure 6:
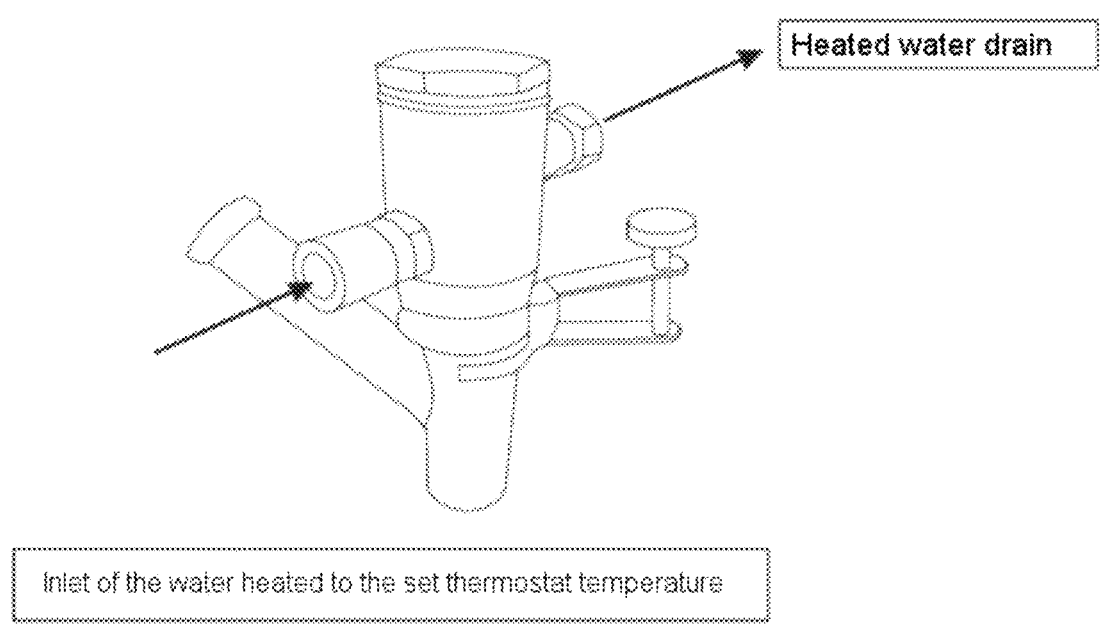

FIG. 6: Graphic representation of the FRANZ cell used in "heat pack" mode.

The invention claimed is:

1. A microneedle array for use in intradermal application comprising a plurality of microneedles on a carrier and the microneedle array has at least one heat-generating element, wherein the microneedles contain a substantially water-soluble formulation and at least one water-soluble polymer which contain at least one active ingredient, wherein the at least one heat generating element is a latent heat store and the heat of the at least one heat-generating element can be held for up to 6 hours.

2. The microneedle array for use in intradermal application according to claim 1, wherein the water-soluble formulation containing at least one active ingredient is present in the tip of the microneedles and/or is part of a coating.

3. The microneedle array for use in intradermal application according to claim 1, wherein the heat is generated after recrystallization from a supersaturated solution i.) by chemical oxidation reaction, or ii.) by physicochemical processes.

4. The microneedle array for use in intradermal application according to claim 1, wherein the heat is generated after recrystallization from a supersaturated solution i.) by chemical oxidation reaction of atmospheric oxygen with pyrophoric iron on activated carbon in the presence of water or ii.) by physicochemical processes, by the release of crystallization heat.

5. The microneedle array for use in intradermal application according to claim 1, wherein the microneedle array contains an electrically conductive, textile fabric in which electrically conductive fibers are in contact with one another and heat can be generated by supplying an external or internal power source.

6. The microneedle array for use in intradermal application according to claim 1, wherein the microneedle array contains an ultrasound transmitter together with an electrically conductive piezo film, and heat can be generated by supplying an external or internal power source.

7. The microneedle array for use in intradermal application according to claim 1, wherein the heat of a heat-generating element is 42-50 degrees Celsius.

8. The microneedle array for use in intradermal application according to claim 1, wherein the penetrated microneedles are at least partially dissolved and resorb in situ under the influence of heat.

9. The microneedle array for use in intradermal application according to claim 1, wherein the water-soluble polymer is selected from the group consisting of polyvinylpyrrolidone, polyvinyl alcohols, cellulose, dextrans, alpha-hydroxy acids, polylactides, polyglycolides, polylactide-co-glycolides, and copolymers thereof.

10. The microneedle array for use in intradermal application according to claim 1, wherein the water-soluble polymer is selected from the group consisting of polyvinylpyrrolidone, polyvinyl alcohols, cellulose, dextrans, lactic acid and/or glycolic acid, polylactides, polyglycolides, polylactide-co-glycolides, and copolymers thereof is selected with polyethylene glycols, polyanhydrides, poly (ortho) esters, polyurethanes, polybutyric acids, polyvaleric acids, and polylactide-co-caprolactones.

11. The microneedle array for use in intradermal application according to claim 1, wherein a density of the microneedles on a carrier is 5-5,000 pieces/cm$^2$.

12. The microneedle array for use in intradermal application according to claim 1, wherein the at least one active ingredient is selected from the group of hypnotics, sedatives, antiepileptics, wake amines, psychoneurotropics, neuromuscular blockers, antispasmodics, antihistamines, antiallergics, cardiotonics, antiarrhythmics, diuretics, hypotensives, vasopressors, antitussives, expectorants, analgesics, thyroid hormones, sex hormones, glucocorticoid hormones, antidiabetics, antitumor agents, antibiotics, chemotherapeutic agents, narcotics, anti-Parkinson agents, anti-Alzheimer's agents, triptans and vaccine scrums.

13. The microneedle array for use in intradermal application according to claim 1, wherein the at least one heat-generating element is designed as a backing layer of the carrier of the microneedle array.

14. The microneedle array for use according to claim 1, wherein the microneedle array has fixing means.

15. The microneedle array for use according to claim 1, wherein the microneedle array has fixing means selected from the group consisting of adhesive strips, plasters, tape, elastic band, rubber and belts.

16. The microneedle array for use according to claim 1, wherein the microneedle array has a reduced lag time when compared to a microneedle array which differs by lack of the at least one heat-generating element.

* * * * *